(12) United States Patent
Schirmer

(10) Patent No.: US 7,064,544 B1
(45) Date of Patent: Jun. 20, 2006

(54) METHOD AND SYSTEM OF SCALING MR SPECTROSCOPIC DATA ACQUIRED WITH PHASED-ARRAY COILS

(75) Inventor: Timo Schirmer, Hallbergmoos (DE)

(73) Assignee: General Electric Company, Schenectady, NY (US)

( * ) Notice: Subject to any disclaimer, the term of this patent is extended or adjusted under 35 U.S.C. 154(b) by 79 days.

(21) Appl. No.: 10/709,613

(22) Filed: May 18, 2004

(51) Int. Cl.
  *G01V 3/00* (2006.01)
  *A61B 5/055* (2006.01)

(52) U.S. Cl. .................... 324/307; 324/310; 600/410
(58) Field of Classification Search ............... None
  See application file for complete search history.

(56) References Cited

U.S. PATENT DOCUMENTS

| | | | | |
|---|---|---|---|---|
| 3,530,373 A | * | 9/1970 | Waugh | 324/311 |
| 3,810,001 A | * | 5/1974 | Ernst | 324/313 |
| 4,385,277 A | * | 5/1983 | Hanley | 324/309 |
| 4,585,992 A | * | 4/1986 | Maudsley et al. | 324/309 |
| 4,665,366 A | * | 5/1987 | Macovski | 324/309 |
| 4,933,844 A | * | 6/1990 | Otvos | 600/419 |
| 4,962,357 A | * | 10/1990 | Sotak | 324/309 |
| 5,192,909 A | * | 3/1993 | Hardy et al. | 324/309 |
| 5,374,889 A | * | 12/1994 | Leach et al. | 324/309 |
| 5,570,019 A | * | 10/1996 | Moonen et al. | 324/309 |
| 5,903,149 A | * | 5/1999 | Gonen et al. | 324/307 |
| 6,037,772 A | * | 3/2000 | Karczmar et al. | 324/309 |
| 6,674,282 B1 | * | 1/2004 | Pines et al. | 324/307 |
| 6,891,371 B1 | * | 5/2005 | Frigo et al. | 324/307 |
| 6,987,997 B1 | * | 1/2006 | Hurd et al. | 600/410 |
| 2001/0024796 A1 | * | 9/2001 | Selifonov et al. | 435/7.1 |
| 2003/0052677 A1 | * | 3/2003 | Pines et al. | 324/307 |
| 2004/0095139 A1 | * | 5/2004 | Brown | 324/309 |

* cited by examiner

*Primary Examiner*—Diego Gutierrez
*Assistant Examiner*—Tiffany A. Fetzner
(74) *Attorney, Agent, or Firm*—Ziolkowski Patent Solutions Group, SC; Michael A. Della Penna; Carl B. Horton

(57) ABSTRACT

The present invention is directed to a system and method of resealing spectroscopic data acquired with phased-array or surface coils to absolute "local" units and, hence, preserves the industry-desirable quantitative approach to single voxel MRS. An MRS signal is acquired from water using a body coil and is used as a reference signal to scale MR spectroscopic data acquired with a plurality of RF receive coils, i.e. phased-array or surface coils. In the resealing process, the amplitude of water in the MRS data will be set to match the amplitude of the water reference signal.

20 Claims, 3 Drawing Sheets

METHOD AND SYSTEM OF SCALING MR SPECTROSCOPIC DATA ACQUIRED WITH PHASED-ARRAY COILS

BACKGROUND OF INVENTION

The present invention relates generally to MR imaging and, more particularly, to a method of scaling MR spectroscopic data acquired with a phased-array or surface coil arrangement. Moreover, the present invention includes a system that supports the acquisition of MR spectroscopic data for quantitative analysis of proton single voxel (volume element) spectra with a receive coil arrangement that also supports the acquisition of MR imaging data.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

MR spectroscopy (MRS) is a common MR technique used for the determination of individual chemical compounds or metabolites located within a volume of interest. The underlying principle of MRS is that atomic nuclei are surrounded by a cloud of electrons which slightly shield the nucleus from any external magnetic field. As the structure of the electron cloud is specific to an individual molecule or compound, the magnitude of this screening effect is then also a characteristic of the chemical environment of individual nuclei. Since the resonance frequency of the nuclei is proportional to the magnetic field it experiences, the resonance frequency can be determined not only by the external applied field, but also by the small field shift generated by the electron cloud. Detection of this chemical shift, which is usually expressed as "parts per million" (ppm) of the main frequency, requires high levels of homogeneity of the main magnetic field $B_0$.

Quantitative analysis of proton single voxel spectra in terms of arbitrary units has become a widely-used and standard approach for carrying out MRS exams. Typically, the quantitative analysis relies or is predicated upon the direct proportionality of acquired MRS signal and metabolite concentrations in the voxel when the MRS signal is scaled by transmitter and receiver gains. This proportionality is particularly accurate for RF signal transmission and reception with linear or quadrature volume resonators or coils. However, such scaling can be inaccurate when the MRS signal is acquired with surface or phased-array coils as a result of the spatially varying $B_1$ sensitivity of these coils.

Phased-array coils are frequently being used to acquire MR imaging data, but not MRS data. MRS data is generally acquired with volume resonators characterized by spatially homogeneous $B_1$ sensitivity. However, a number of imaging techniques, including parallel imaging, require phased-array coil arrangements. In addition, other imaging techniques prefer phased-array coil arrangements because these arrangements advantageously combine the preferred SNR characteristics of smaller FOV coils with the extended FOV coverage afforded by larger volume resonators. As noted above, however, it is impractical to use phased-array coils to acquire MRS data in order to carry out a quantitative analysis of proton single voxel spectra. To conduct an MR imaging scan with parallel imaging techniques as well as acquire MRS data for quantitative analysis requires a change between phased-array coils and volume resonators during the clinical exam—a time consuming, arduous, and impractical task.

Other proposed approaches to rescaling MRS data acquired with phased-array or surface coils utilize coil sensitivity maps. Generation of coil sensitivity maps, however, requires separate imaging scans—a scan to acquire the MRS data and a scan to acquire coil sensitivity data. Separate scans decrease patient throughput and are therefore not a viable solution.

It would therefore be desirable to have a system and method capable of quantitative MRS analysis of MR spectroscopic data acquired with a phased-array or surface coil arrangement.

BRIEF DESCRIPTION OF INVENTION

The present invention provides a system and method of scaling MRS data acquired with a phased-array or surface coil arrangement to support proton single voxel spectra quantitative analysis that overcomes the aforementioned drawbacks.

The present invention includes a system and method capable of rescaling spectroscopic data acquired with phased-array or surface coils to absolute "local" units and, hence, preserves the quantitative approach to single voxel MRS. A reference signal that is acquired with a body RF coil from a volume-of-interest (VOI) is used to scale MR spectroscopic data acquired from the VOI with a plurality of RF receive coils, i.e. phased-array or surface coils. In this regard, the amplitude of the reference signal and the amplitude of a corresponding signal in the MRS data are matched. For instance, unsuppressed water across the VOI may be used as the reference signal. In the rescaling process, the amplitude of water in the MRS data will be set to match the amplitude of the water reference signal.

Therefore, in accordance with one aspect of the present invention, a method of MRS includes the steps of acquiring a reference signal with a body coil and acquiring metabolite signals with a plurality of receive coils. The method further includes combining the metabolite signals to form a single MRS spectrum and scaling the single MRS spectrum as a function of intensity of the reference signal.

In accordance with another aspect of the invention, an MRI apparatus includes an MRI system having a plurality of gradient coils positioned about a bore of a magnet to impress a polarizing magnetic field. An RF transceiver system and an RF switch are controlled by a pulse module to transmit and receive RF signals to and from an RF coil assembly to acquire MRS data. The RF coil assembly includes a body RF volume coil for RF transmission and reception, and a phased-array of RF coils for RF reception. The MRI apparatus also includes a computer programmed to scale a composite signal of metabolite signals acquired with the phased array coils based on a reference signal acquired with the whole body coil.

In accordance with another aspect, the invention is embodied in a computer program stored on a computer readable storage medium and having instructions which, when executed by a computer, cause the computer to acquire an unsuppressed MRS water signal with a transmit and receiver volume coil, and acquire MRS metabolite signals with a plurality of receive coils. The computer is then caused to combine the MRS metabolite signals to form an MRS composite spectrum and scale the MRS composite spectrum to an intensity of the unsuppressed MRS water signal.

Various other features, objects, and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

Figure 1:
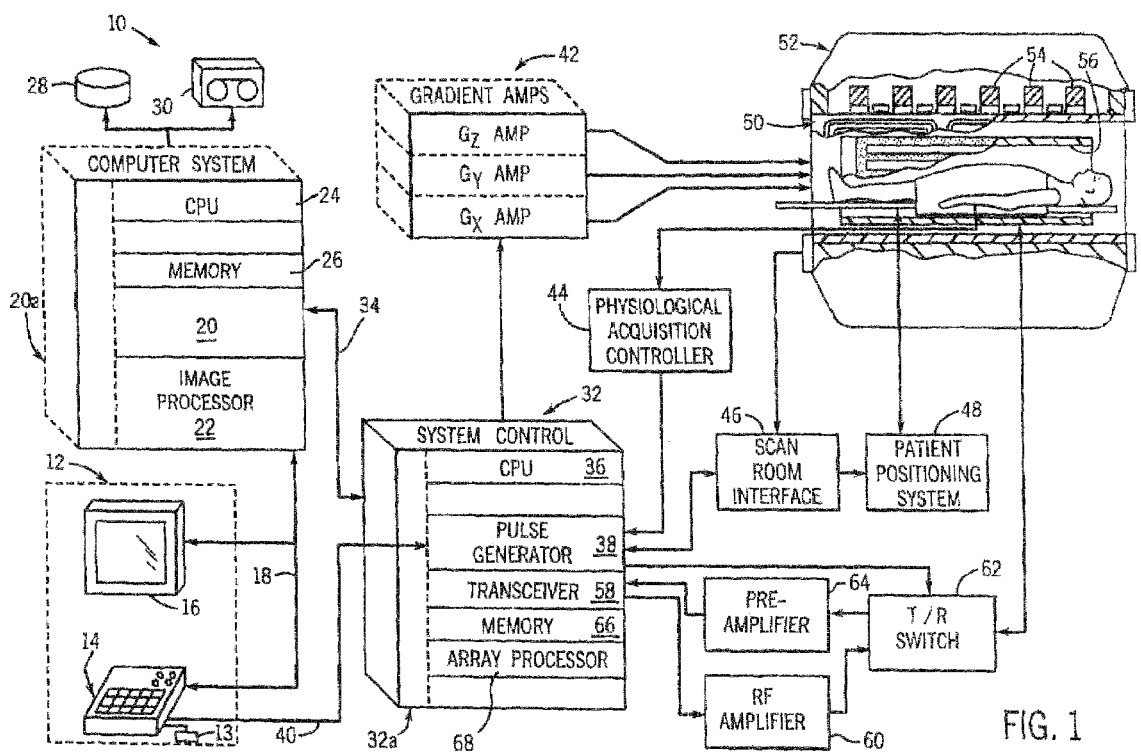
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image or spectrum to be reconstructed, and each of these is input to an array processor 68 which operates to Fourier transform the data into an array of image or spectroscopy data. This image or spectroscopy data is conveyed through the serial link 34 to the computer system 20 where it is stored in memory, such as disk storage 28. In response to commands received from the operator console 12, this image or spectroscopy data may be archived in long term storage, such as on the tape drive 30, or it may be further processed by the image processor 22 and conveyed to the operator console 12 and presented on the display 16.

The present invention is directed to a system and method of obtaining absolute scaling of metabolite signals acquired with phased-array or surface coils in a single voxel MR spectroscopic exam. The acquisition of the required data can easily be integrated into a standard spectroscopy exam. For a clinical exam, the present invention allows a spectroscopy exam aiming for absolute quantification to be added or otherwise incorporated with a standard clinical MR imaging exam without needing to consider changing the coil from a phased-array to a quadrature volume resonator during the patient study.

The present invention is particularly applicable with a 1.5T MRI scanner such as a GE Signa® LX scanner that is commercially available from GE Healthcare, Waukesha, Wis., but is applicable with other MR scanners. SIGNA is a registered trademark of General Electric Company, Fairfield, Conn. As will be described, MR spectroscopy data is acquired with a multi-channel phased-array coil whereas reference data is acquired with a body coil. The body coil may be a whole-body coil or a partial body coil, and the present invention is equivalently applicable with each. While it is common to use a body coil as transmitter in combination with phased-array coils, the present invention also uses the body coil to receive reference data. The use of phased-array coils has been chosen as an example, but one skilled in the art will appreciate that the present invention is applicable with other types of surface or array coils. A Point REsolved SpectroScopy (PRESS) based single voxel technique may be used for data acquisition but other localized spectroscopy sequences are equivalently applicable. While the present invention will be described with respect to single voxel spectra, the present invention is equivalently applicable to chemical shift imaging (CSI) data and the like.

Figure 2:
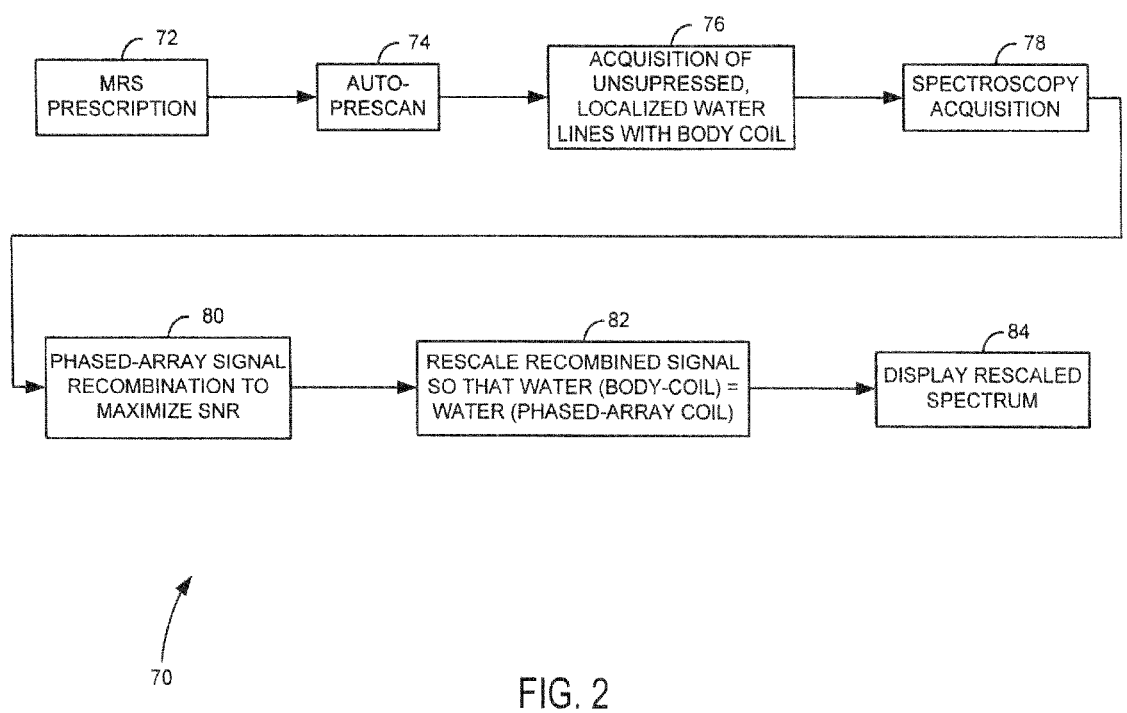
FIG. 2 is a flow chart setting forth the steps of an MRS acquisition and resealing technique in accordance with the present invention.

Referring now to FIG. 2, the steps of a technique 70 to α-quire and reconstruct single voxel MR spectra are set forth. The MRS exam 70 begins with prescription of the MRS exam, placement of the patient or other subject in the MR scanner, and executing standard pre-scanning protocols well-known in the art 72. After the subject is properly positioned and the MRS prescription set 72, as in most standard MR spectroscopy scans, an automatic pre-scan is carried out at 74. The data acquired from the pre-scan is used to calibrate or otherwise set scan parameters such as shim values, transmit frequencies, receiver gains of the phased-array coil arrangement, and the transmitter gain of the body coil. In contrast to the acquisition of spectroscopic data after the prescan of a standard MRS exam, MRS technique 70 of the present invention continues with acquisition at 76 of a reference signal 86, FIG. 3. This reference signal 86, as will be described, will be used to scale MRS data acquired with the phased-array or surface coils.

It is contemplated that a number of substances may be used as the basis of the target signal, but in a preferred embodiment, the reference signal is acquired at 76 from unsuppressed, localized water lines. It should be noted that the reference signal is acquired with the body coil. In this regard, the body coil is used to transmit as well as receive RF energy. The reference signal is also acquired from the same VOI from which the MRS data will be acquired.

Following acquisition of the reference signal at 76 a spectroscopy acquisition is carried out whereby MRS data is acquired from the phased-array or surface coil arrangement at 78 in a known manner. A PRESS-based or other acquisition process may be used to acquire the MRS data. In known MRS, the spectroscopy data acquisition with phased array coils is customarily followed by an individual reconstruction and a final recombination of these spectra to produce a single spectrum with maximized SNR. As a result, the signal amplitude of the resulting spectrum is not directly proportional to the metabolite concentrations in the volume element studied due to scaling factors applied during the recombination algorithm and the spatially varying reception profile of the phased array coils.

To re-gain this proportionality, process 70 follows the acquisition of the MRS data with the recombination of the MRS data acquired from the respective coils of the phased-array or surface coil arrangement to a single recombined MRS signal 80. This recombination not only yields a single MRS signal or spectrum, but the recombination is carried out to maximize or otherwise improve SNR. Following recombination, the recombined MRS signal or spectrum is rescaled 82 as a function of the intensity of the reference signal. In a preferred embodiment, the recombined MRS signal is rescaled such that the portion of the combined spectrum that is associated with water has the same amplitude as the reference signal. That is, the combined signal is scaled such that the amplitude of the water signal acquired with the whole body coil matches the amplitude of the water signal acquired with the phased-array or surface coil arrangement. As a result, a scaled spectrum may be displayed at 84 for a given volume element with a direct proportionality being reclaimed between metabolite concentration in the volume and the acquired MRS signal.

As heretofore described, the MRS data acquired with the phased-array or surface coil arrangement is scaled by a reference signal acquired by a body coil. As such, the phased-array or surface coils are collectively adjusted to have a sensitivity to the VOI as the body coil, which spatially covers the VOI.

Figure 3:
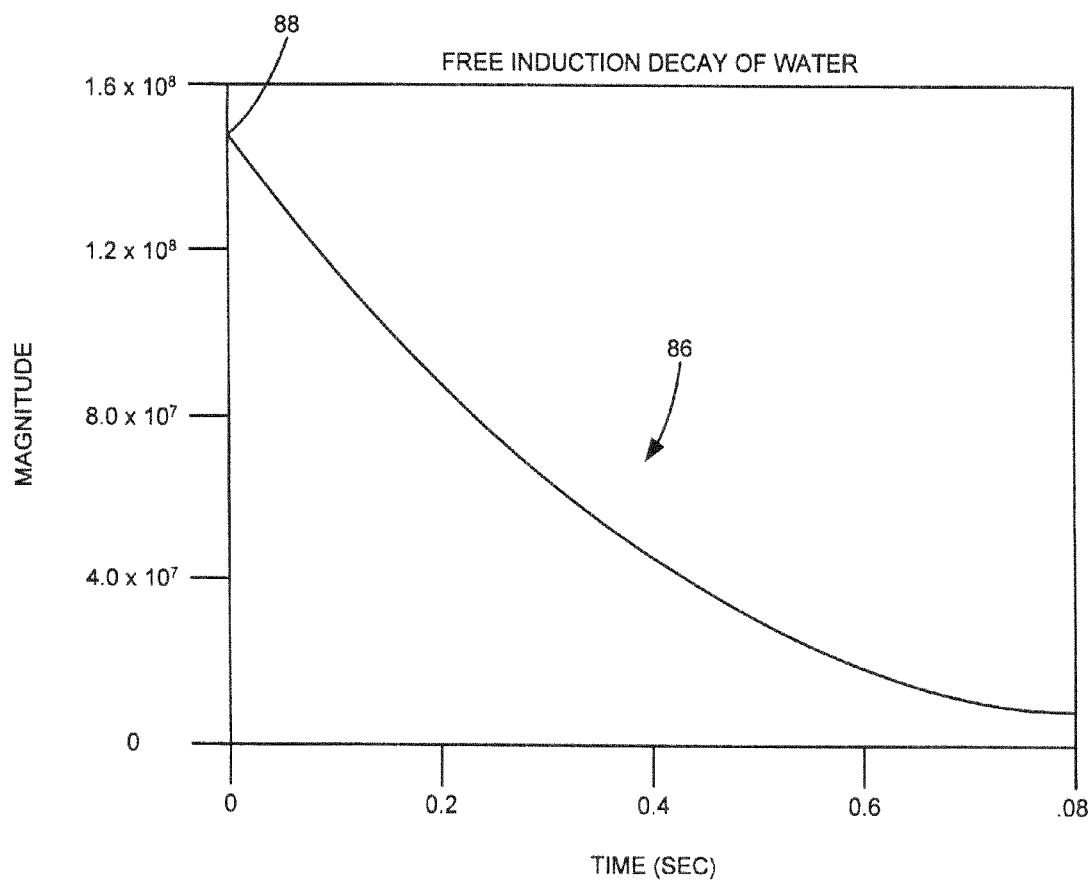
FIG. 3 is a graph illustrating an exemplary free induction decay (FID) curve of unsuppressed water signal acquired with a body coil used as a transmit and receive coil.

Referring now to FIG. 3, a curve 86 indicative of the signal intensity of unsuppressed water over time is shown. Specifically, curve 86 illustrates the free induction decay (FID) of water. This exemplary FID of water is typical for a water signal acquired with a body coil as a transmit and receive coil. As noted above, water may be used as the basis of the reference signal for scaling of the MRS data acquired with the phased-array or surface coils. While any point along the curve may be used, the first point 88 of the FID curve 86 has been shown to provide very reliable results. One skilled in the art will however appreciate that other methods may be used to quantify signal amplitudes.

The present invention has been described with respect to a system and method designed to rescale spectroscopic data acquired with phased-array or surface coils to absolute "local" units and, hence, preserves the industry-preferred, quantitative approach to single volume element MRS. An MRS signal is acquired from water using a whole-body coil and is used as a reference signal to scale MR spectroscopic data acquired with a plurality of RF receive coils, including phased-array or surface coils. In the rescaling process, the amplitude of water or other reference compound, molecule, etc. in the MRS data will be set to match the amplitude of the water or other compound, molecule, etc. reference signal.

As the present invention supports an MRS exam with absolute signal scaling of spectroscopic data acquired with phased-array coils, the present invention further supports implementation of such an MRS exam in conjunction with a conventional MR imaging scan. That is, there is no longer a need to replace the phased-array coil or surface coil architecture used to acquire MR data for imaging with a quadrature or volume resonator previously required for quantitative MRS analysis. An advantage of this invention is that both the MRS analysis and the MR imaging scan can be carried out with the same MR scanner and phased-array or surface coil arrangement. In addition, the present MRS technique described above may be incorporated with standard MRS protocols.

Therefore, a method of MRS is disclosed and includes the steps of acquiring a reference signal with a body coil and acquiring metabolite signals with a plurality of receive coils. The method further includes combining the metabolite signals to form a single MRS spectrum and scaling the single MRS spectrum as a function of intensity of the reference signal.

In another embodiment of the invention, an MRI apparatus includes an MRI system having a plurality of gradient coils positioned about a bore of a magnet to impress a polarizing magnetic field. An RF transceiver system and an RF switch are controlled by a pulse module to transmit and receive RF signals to and from an RF coil assembly to acquire MRS data. The RF coil assembly includes a body RF coil and a phased-array of RF coils. The MRI apparatus also includes a computer programmed to scale a composite signal of metabolite signals acquired with the phased array coils based on a reference signal acquired with the body coil.

In yet another embodiment, the invention is embodied in a computer program stored on a computer readable storage medium and having instructions which, when executed by a computer, cause the computer to acquire unsuppressed MRS water signal with a transmit and receiver volume coil and acquire MRS metabolite signals with a plurality of receive coils. The computer is then caused to combine the MRS metabolite signals to form an MRS composite spectrum and scale the MRS composite spectrum to an intensity of the unsuppressed MRS water signal.

The present invention has been described in terms of the preferred embodiment, and it is recognized that equivalents, alternatives, and modifications, aside from those expressly stated, are possible and within the scope of the appending claims.

What is claimed is:

1. A method of MR spectroscopy (MRS) comprising the steps of:
   acquiring a reference signal with a body coil;
   acquiring metabolite signals with a plurality of receive coils;
   combining the metabolite signals to form a single MRS spectrum; and
   scaling the single MRS spectrum as a function of intensity of the reference signal.

2. The method of claim 1 wherein the step of acquiring the reference signal includes the step of acquiring signal from unsuppressed water with a uniform $B_1$ body coil.

3. The method of claim 1 wherein the plurality of coils is a phased-array coil arrangement.

4. The method of claim 1 further comprising the step of carrying out a pre-scan prior to acquisition of the reference signal.

5. The method of claim 4 further comprising the step of determining at least one of shimming, transmit frequency, receive coil gains, and transmitter gain from the pre-scan.

6. The method of claim 1 wherein the step of scaling includes determining a ratio of reference signal amplitude to single MRS spectrum amplitude and modifying the single MRS spectrum by the ratio.

7. The method of claim 1 further comprising using a phased-array volume coil arrangement for a spectroscopy examination in conjunction with an MR imaging examination.

8. An MRS apparatus comprising:
   a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MRS data, the RF coil assembly having phased array coils and a body coil; and
   a computer programmed to scale a composite signal of metabolite signals acquired with the phased array coils based on a reference signal acquired with the body coil.

9. The MRS apparatus of claim 8 wherein the computer is further programmed to determine an intensity of the reference signal and an intensity of the composite signal, and determine an intensity ratio therefrom.

10. The MRS apparatus of claim 9 wherein the computer is further programmed to modify the composite signal by the intensity ratio.

11. The MRS apparatus of claim 8 wherein the computer is further programmed to scale the composite signal such that signal intensity of water as determined from MRS data acquired by the whole body coil equals signal intensity of water as determined from MRS data acquired by the phased array coils and represented in the composite signal.

12. The MRS apparatus of claim 8 wherein the computer is further programmed to combine metabolite signals respectively acquired from each coil of the phased array coils to form the composite signal and combine the metabolite signals in an SNR increasing manner.

13. The MRS apparatus of claim 8 wherein the computer is further programmed to generate and display an MRS spectrum from the scaled composite signal.

14. The MRS apparatus of claim 13 wherein the computer is further programmed to display the MRS spectrum for a single voxel of a VOI from which the metabolite signals are acquired.

15. A computer readable storage medium having a computer program stored thereon to perform an MRS exam and representing a set of instructions that when executed by a computer causes the computer to:
   acquire unsuppressed MRS water signal with a transmit and receiver coil;
   acquire MRS metabolite signals from a plurality of receive coils;
   combine the MRS metabolite signals to form an MRS composite spectrum; and
   scale the MRS composite spectrum to an intensity of the unsuppressed MRS water signal.

16. The computer readable storage medium of claim 15 wherein the computer is caused to scale the MRS composite signal such that the amplitude of the MRS water signal equals the amplitude of a water signal in the MRS composite spectrum.

17. The computer readable storage medium of claim 15 wherein the plurality of coils is a phased-array volume coil arrangement.

18. The computer readable storage medium of claim 15 wherein the computer is further caused to carry out a pre-scan prior to acquisition of the reference signal.

19. The computer readable storage medium of claim 15 wherein the computer is further caused to determine at least one of shimming, transmit frequency, receiver gain, and transmitter gain from the pre-scan.

20. The computer readable storage medium of claim 15 wherein the computer is further caused to acquire data of a spectroscopy examination using a phased-array volume coil arrangement in conjunction with an MR imaging examination.

* * * * *

UNITED STATES PATENT AND TRADEMARK OFFICE
CERTIFICATE OF CORRECTION

PATENT NO. : 7,064,544 B1
APPLICATION NO. : 10/709613
DATED : June 20, 2006
INVENTOR(S) : Timo Schirmer Page 1 of 1

It is certified that error appears in the above-identified patent and that said Letters Patent is hereby corrected as shown below:

On the cover page, col. 2, paragraph (57) (ABSTRACT), line 2, delete "resealing" and substitute therefore -- rescaling --; and On the cover page, col. 2, paragraph (57) (ABSTRACT), line 8, delete "resealing" and substitute therefore -- rescaling --.

Signed and Sealed this

Nineteenth Day of September, 2006

JON W. DUDAS
*Director of the United States Patent and Trademark Office*